(12) United States Patent
Verlinden et al.

(10) Patent No.: US 7,590,609 B2
(45) Date of Patent: Sep. 15, 2009

(54) EXPERT SYSTEM FOR MEDICAL DIAGNOSIS

(75) Inventors: Stefan Frederik Franciscus Verlinden, Leiden (NL); Hendrikus Johannes Verlinden, Leiden (NL)

(73) Assignee: Vivici B.V., Leiden (NL)

( * ) Notice: Subject to any disclaimer, the term of this patent is extended or adjusted under 35 U.S.C. 154(b) by 269 days.

(21) Appl. No.: 10/494,146

(22) PCT Filed: Oct. 31, 2002

(86) PCT No.: PCT/EP02/12196

§ 371 (c)(1),
(2), (4) Date: Apr. 29, 2004

(87) PCT Pub. No.: WO03/038727

PCT Pub. Date: May 8, 2003

(65) Prior Publication Data

US 2005/0015352 A1    Jan. 20, 2005

(30) Foreign Application Priority Data

Nov. 1, 2001   (NL) .................................... 1019277

(51) Int. Cl.
*G06N 5/02*   (2006.01)
*G06N 5/04*   (2006.01)
(52) U.S. Cl. ........................................................ 706/46
(58) Field of Classification Search ................... 706/46, 706/45

See application file for complete search history.

(56) References Cited

U.S. PATENT DOCUMENTS

| | | | | |
|---|---|---|---|---|
| 4,945,476 A | * | 7/1990 | Bodick et al. | 600/301 |
| 4,970,657 A | * | 11/1990 | Wolf | 706/52 |
| 5,805,160 A | * | 9/1998 | Yoshida et al. | 714/25 |
| 5,911,132 A | | 6/1999 | Sloane | |
| 6,022,315 A | * | 2/2000 | Iliff | 600/300 |
| 6,234,964 B1 | | 5/2001 | Iliff | |

FOREIGN PATENT DOCUMENTS

| | | |
|---|---|---|
| WO | WO 00/41613 A2 | 7/2000 |
| WO | WO 00/41613 A3 | 7/2000 |
| WO | WO 01/61616 A2 | 8/2001 |
| WO | WO 01/61616 A3 | 8/2001 |

* cited by examiner

*Primary Examiner*—David R Vincent
*Assistant Examiner*—Nathan H Brown, Jr.
(74) *Attorney, Agent, or Firm*—Lahive & Cockfield, LLP; Kevin J. Canning

(57) ABSTRACT

An expert system, in particular for medical diagnosis, includes a memory 2 for storing a plurality of hypotheses. The hypotheses are arranged in a first and second disjoint group of hypotheses. The memory stores questions for rejecting hypotheses of the second group. An output 3 is used for supplying questions to a user. A input 4 is used for receiving initial data and answers to questions. A processor 5 is programmed to select questions from the stored questions for those hypotheses from the second group that are possible in dependence on the initial data. The processor also determines from answer(s) received in response to outputting the selected questions whether at least one of the hypotheses of the second group is possible. In response to determining that no hypothesis of the second group is possible, the processor supplies a most likely hypothesis of the first group.

14 Claims, 2 Drawing Sheets

EXPERT SYSTEM FOR MEDICAL DIAGNOSIS

RELATED APPLICATIONS

This application is a 35 U.S.C. 371 national stage filing of International Application No. PCT/EP02/12196, filed 31 Oct. 2002, which claims priority to Patent Application No. 1019277 filed on 1 Nov. 2001 in The Netherlands. The contents of the aforementioned applications are hereby incorporated by reference.

FIELD OF THE INVENTION

The invention relates to an expert system, in particular for medical diagnosis.

BACKGROUND OF THE INVENTION

Huge libraries have been compiled with questions for symptoms relating to diseases. Known expert systems for medical diagnosis can use these libraries to phrase questions and based on the questions calculate the likelihood of the diseases. To come to a reliable diagnosis the number of questions to be put is too high for practical use. Using only a limited number of questions in the known system makes the chance of overlooking a possible serious disease too high. This can cause liability issues. Therefore, the known systems evaluate all possible diseases fully, making the systems impractical and user unfriendly.

It is an object of the invention to provide a user friendly expert system, in particular a medical diagnosis system, that with a limited number of interactions with a user can confirm a hypothesis (e.g. make a diagnosis) without risking overlooking hypotheses that may not be taken by the system or can not be taken with the limited number of interactions.

SUMMARY OF THE INVENTION

To meet the object of the invention, an automatic expert system includes: a memory for storing a plurality of hypotheses, where the hypotheses are arranged in at least a first and second disjoint group of hypotheses; and for storing questions for rejecting hypotheses of the second group; an output for supplying questions from the memory; an input for receiving initial data and answers to outputted questions; a processor programmed to select questions from the stored questions for those hypotheses from the second group that are possible in dependence on the initial data; determine from answer(s) received in response to outputting the selected questions whether at least one of the hypotheses of the second group is possible; and in response to determining that no hypothesis of the second group is possible, supply via the output a most likely hypothesis of the first group in dependence on at least the initial data.

According to the invention hypotheses are divided into two disjoint groups. The system tests the hypotheses of the second group with the aim of rejecting those hypotheses. Having successfully rejected all those hypotheses, the system provides as an outcome a most likely one of the hypotheses of the first group. In general, it is easier to reject a hypothesis than to confirm a hypothesis, implying that fewer questions need to be asked. For example, the hypothesis "this person is healthy" can be rejected if a question like "Coughing blood?" is answered affirmatively, without knowing exactly what the exact cause of this symptom is. The same holds for a complex of symptoms. Fewer questions can used, since it is not required that the system issues a positive diagnosis for hypothese it only needs to rule out. The system has to check whether symptoms that are suspicious for at least one of the selected hypotheses of the second group are present. If this is the case, the system can not rule a hypothesis of the second group out and, generally, the user will be referred to a human expert. After rejecting all hypotheses of the second group, the system issues the most likely diagnosis of the first group based on at least the initial data supplied by the user. In many practical implementations the second group of hypotheses can be significantly smaller than the first group. Additionally, the initial data aids in narrowing down the hypotheses to be rejected. Since all selected hypotheses of the second group need to be thoroughly checked, the number of thorough tests can be relatively small. As an example, in a system that can issue 30 different questions and allows for each question two different answers in total $2^{30}(=1E9)$ different answer sequences are possible. In a conventional system each of these sequences is coupled to an end conclusion (a label, or confirmation of a certain hypothesis). In the system according to the invention, only a subset of hypotheses must be checked. If they are all rejected, in principle the most likely hypothesis can be confirmed. In the exemplary system typically only 1E4 answer sequences lead to rejection of the most likely hypothesis. If the same number of questions were still used for rejecting these hypotheses, the number of fully coded answer sequence would be reduced by a factor of 1E5. In reality, the number of questions can also be significantly smaller, leading to an even further reduction in possible answer sequences. This saves a significant amount of memory and increases speed during the evaluation of the given answers.

It should be noted that also electronic medical encyclopedia are known that enable the user to specify a complaint and provide further details regarding the complaint. The electronic encyclopedia uses this data to select electronic articles of interest to the user. Such systems are not designed to confirm or reject hypotheses. The number of complaints and additional data the user can specify for a complaint is preprogrammed. The number of questions is limited and targeted towards most common ailments. As such these systems are unsuitable for reliably confirming or reacting hypotheses. In particular, for medical diagnosis such an approach has an unacceptably high chance of overlooking a harmful pathology.

In a preferred embodiment as described in the dependent claim 2, the expert system is used for medical diagnosis; tho initial data including a health complaint; and the processor being programmed to select the questions in dependence on the health complaint. The concept of an expert system wherein based on an initial hypothesis the questions are targeted towards testing a selection of alternatives (not all possible hypothesis) can also be used for other applications then medical diagnosis. By only having to eliminate a small subset of hypotheses the system is simpler, faster, and safer for use as a front-end for a human expert that only deals with the more complicated cases.

As described in the dependent claim 3, the first group of hypotheses includes hypotheses that may be taken by the system and the second group includes hypotheses that may not be taken by the system. For medical diagnosis, the second group typically contains all diagnoses that are potentially harmful and require the attention of a medical expert. The first group contains the remaining diagnoses that the system may take. Typically, This includes the diseases that do not require any attention or can be cured/treated by the user without any further assistance of a medical expert. The new expert system according to invention eliminates symptoms/complexes of symptoms that are suspicious for harmful ailments instead of fully evaluating all possible diagnoses from the first and second group and determining a most likely diagnosis. As an example, an evaluation involving 11092 patients with an initial complaint of coughing (supplied as initial data by the user) showed the top 20 diagnoses that in fact cover almost all likely diagnoses. Of those 20 diagnoses, seven fall into the first group according to the invention and have to be eliminated (those ailments include: asthma, pneumonia, chronic bronchitis, emphysema, whooping cough and heart failure). Preferably, at least those seven hypotheses need to be rejected (and thus possibly evaluated in more detail) before in principle a diagnosis can be given safely. Some more diagnoses that are not in the top 20 may be added to the list of hypotheses to be rejected if such a diagnosis, although very rare, is considered urgent (e.g. very high fever). As indicated above, in principle a hypothesis can be rejected if none of the symptoms are present that must be checked by a human expert. The hypothesis does not need to be confirmed. To rule out the hypothesis "asthma" a few symptoms, such as breathlessness during the evening/night, breathing with peeping, etc. need to be checked. If any of such symptoms is present the hypothesis can not be rejected (and advice of a medical expert may be required).

As described in the dependent claim 4, the processor is programmed to determine whether at least one of the hypotheses of the second group is possible by comparing received answers to a predetermined answer sequence stored in or derivable from the memory. Comparing a sequence of received answers with stored predetermined answer sequence(s) is an effective way of determining whether a hypothesis is possible.

As described in the dependent claim 5, the memory stores for each hypothesis of the second group a respective associated question set for rejecting the hypothesis and the processor is programmed to select all hypotheses from the second group that are possible in dependence on the initial data and to perform the selection of questions by combining question sets of selected hypotheses of the second group. In this way, automatically a list of questions is compiled from predetermined sets of questions, where each set of question is optimized for rejected a respective hypothesis.

As described in the dependent claim 6, the processor is programmed to supply via the output an indication that no hypothesis can be made in response to determining that at least one hypothesis of the second group is possible. If at least one of the hypotheses of the second group can not be rejected by the system (e.g. this would be too risky or would require too many detailed questions), the system informs the user that it can not take a positive hypothesis.

As described in the dependent claim 7, the processor is programmed to terminate outputting questions in response to determining that at least one hypothesis of the second group is possible. The elimination of the selected hypotheses of the second group stops as soon as the system comes to the conclusion that it can not rule out that this hypothesis is possible. The system can then not take a decision and there is no need for asking further details from the user.

As described in the dependent claim 8, the memory stores for at least one hypothesis of the first group a respective associated question set for confirming the hypothesis; and the processor is programmed to, in response to determining that no hypothesis of the second group is possible, and the most likely hypothesis of the first group is associated with a question set output questions of the associated question set; determine whether the most likely hypothesis meets a predetermined criterion in dependence on at least one further answer; and provide an outcome of the determination. After having eliminated the hypotheses of the second group, the system is able to further test a most likely hypothesis of the first group. This improves the quality. In general there is no need to thoroughly test all other hypotheses of the first group since the hypotheses of the first group can be taken safely.

As described in the dependent claim 9, the memory stores for at least one hypothesis of the second group a respective associated further question set for confirming the hypothesis; and the processor is programmed to, in response to determining that the hypothesis of the second group is possible: output questions of the associated question set; determine whether the hypothesis of the second group meets a predetermined criterion in dependence on at least one further answer; and provide an outcome of the determination. If after a first test, the system comes to the conclusion that a hypothesis of the second group is possible, the system is able to further test the hypothesis, particularly with the aim of collecting more data for confirming the hypothesis and supply to a medical expert.

In a preferred embodiment, the system can share questions between hypotheses. If an answer to a question has already been received (during testing of an earlier hypothesis), the question can be skipped during the testing of a subsequent hypothesis, reducing the number of interactions with the user. As an example, initial data specifying a complaint of a running nose may give an ordinary nose cold (rhinitis) as a most likely hypothesis from the first group and tries to eliminate hay fever (allergic rhinitis) as an hypothesis of the second group. While eliminating the latter hypothesis, the questions to answers testing this hypothesis may show that sinusitis (a hypothesis of the first group) is likely and should, preferably, be tested next. The system switches then to the question set for testing this hypothesis. Normally, this question set will also include the question(s) for evaluating hay fever. Since answers for these questions have already been received, these questions can be skipped from the set. Preferably, the system can also share possible answers between questions of different question sets (i.e. different hypotheses). This enables using an already received answer also for evaluating other hypotheses. As an example, the specific symptom cough in combination with the fact that this occurs 3 times or more a year in a person who is over the age 40 and who smokes, makes it very likely that this person suffers from Chronic Obstructive Pulmonary Disease (COPD).

As described in the dependent claim 10, the processor is programmed to update the selection of questions during testing of the questions in dependence on received answer(s). The system continuously updates the list of questions (i.e. hypotheses to be rejected) in dependence on input from the user, such as the initial data and/or answers to questions. The outcome of a test of a hypothesis may also result in removing other hypotheses from testing. On the other hand, an answer given to a hypothesis may make it necessary to evaluate other hypotheses as well. Although in principle the list of hypotheses to be rejected should be reliable, an answer to a question may overrule data already received by the same, e.g. the user may have provided wrong or conflicting answers.

As described in the dependent claims 11 and 12, the system rejects or confirm hypotheses based on initial data supplied to the system and/or answers to earlier questions.

As described in the dependent claim 13 and 14, the system can transfer control to a human expert, e.g. when a hypothesis of the second group is possible or confirmed As described in the dependent claim 15, the system can retrieve data from a medical record storing system and use data from this record for its operations and/or store data in the medical record. Preferably, this includes at least one of the following:

- using the data to select the hypotheses to be rejected (second group),
- using the data to select the hypotheses to be confirmed (first group),
- using the data to retrieve answers to question(s) of the question set being tested,
- storing the initial data in the medical record,
- storing received answer in the medical record,
- storing in the medical record hypotheses of the second group that can not be ruled out, or
- storing in the medical record a most likely hypothesis of the first group.

To meet an object of the invention, a computer program product is operative to cause a processor to perform the steps of: receiving initial data via an input; selecting from a memory that stores a plurality of hypotheses, where the hypotheses are arranged in at least a first and second disjoint group of hypotheses, and that stores questions for rejecting hypotheses of the second group, questions for those hypotheses from the second group that are possible in dependence on the initial data; determining from answer(s) received in response to outputting the selected questions whether at least one of the hypotheses of the second group is possible; and in response to determining that no hypothesis of the second group is possible, supplying via the output a most likely hypothesis of the first group in dependence on at least the initial data.

These and other aspects of the invention are apparent from and will be elucidated with reference to the embodiments described hereinafter.

DETAILED DESCRIPTION OF THE PREFERRED EMBODIMENT

Figure 1:
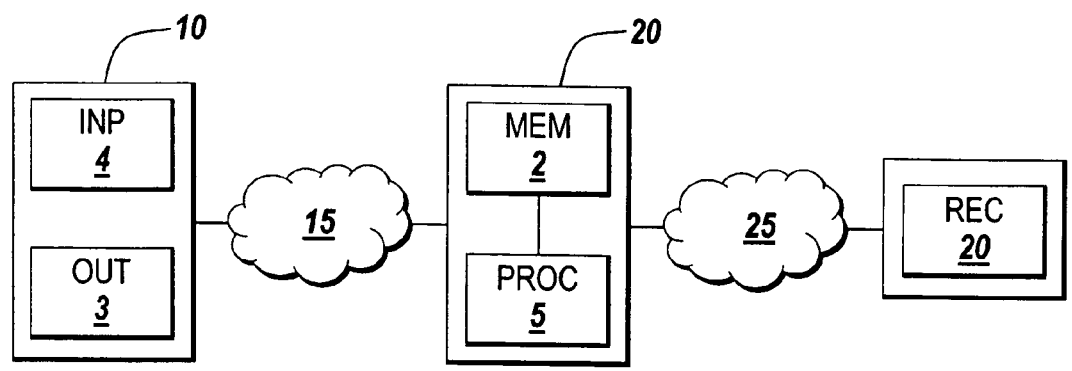
FIG. 1 shows a block diagram of the system according to the invention.

The expert system according to the invention will be described focusing on medical diagnosis. It will be appreciated that the described technique can be used for any expert system, in particular those with a relatively high number of hypotheses to be tested and where certain hypotheses must be rejected before other hypotheses may be taken. As an example, an expert system including expert knowledge on a chemical process may include some hypotheses that must have been rejected since the consequences of overlooking the hypothesis may be too severe (e.g. danger of an explosion) even if the chance of this hypothesis being the case is very low. Thn expert system according to the invention can also be used by governmental institute for checking whether a person/company is entitled to subsidy. Using the initial data, the system can determine from a large collection of possible subsidies a most likely one that meets the initial data. The system then aims to test all negative situations (hypotheses) which may make it impossible to obtain the subsidy. If none of the tested hypotheses apply, in principle the user can signaled that a subsidy can be requested. Not all possible subsidies that are possible need to be evaluated. It may be sufficient that it is confirmed that the most likely subsidy seems possible. A similar system can be used for verifying whether a user can apply for a loan or mortgage. In general the system is suitable for, based on initial data, determining a most likely hypothesis that may be given by the system and via questions eliminate all possible alternative hypotheses that may not be given by the system. The most likely hypothesis is then only given if all of these alternative hypotheses have been rejected. The outcome of the system can thus be a confirmed hypothesis, such as a medical diagnosis. This may also take the form of an advice (e.g. recommended subsidy or product to buy).

Before going into detail of the invention, first an example is given for a medical diagnosis system. Assuming that a complaint of a user is a cough, the system may determine that the most likely diagnosis is: ordinary head cold (i.e. most likely one of all diagnoses matching the initial data and not needing further medical attentions). Instead of trying to test all hypotheses, the system retrieves list of alternative diagnoses that do need medical attention (and thus need to be eliminated). It compiles a list of questions to test these diagnoses and issues the questions to the user. Example: if the ankles are swollen (edema) it is not safe to put the diagnosis of an ordinary head cold. So, the question is put whether the ankles are swollen (can usually be checked by the patient by seeing whether the sock edges have given in imprint on the lower leg). If the answer is yes, the initial diagnosis can not be made a safely. The system may exit or try to positively confirm a more serious disease (in this example, this combination of cough and swollen ankles is suspicious for a heart failure).

Figure 2:
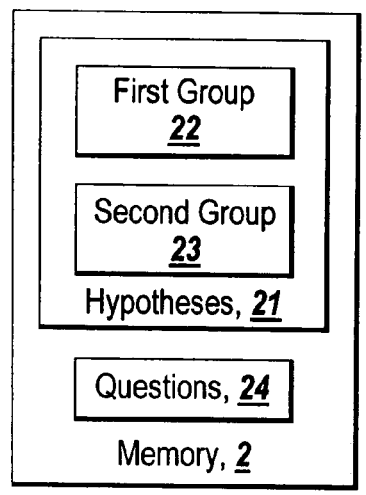
FIG. 2 is an exemplary block diagram of the storage depicted in FIG. 1.

FIG. 1 shows a block diagram of a system according to the invention. The core functionality of the system is typically provided by a computer application (software) executed on any suitable computer, such as a standalone computer or a server in a network like the Internet. The system includes a storage 2 for storing a collection of questions (24 in FIG. 2). The storage is preferably a non-volatile memory, such as a hard disk. More details on the arrangement of the questions will be provided below. Output 3 enables the system to represent the stored questions to a user. The output is also used for giving diagnoses, conclusions to a user and/or human expert. If so desired, the system may have several outputs. The output may take any suitable form, such as a display for displaying the questions and answers provided by the user. The output may also be in a spoken form, e.g. via a telephone or generated via the speakers of a computer. In this case, the spoken messages may, for example, have been pre-recorded in the system or on-line synthesized in any suitable way. The output may also be in other forms, such as via paper. The system includes an input 4 for receiving input from a user, including initial data (such as a medical complaint) and answers to questions issued by the system. The input may take the form of a keyboard for receiving the initial data, such as medical complaint, and/or personal data including age, gender, sex, and (if desired) name, address, medical insurance number, etc. The input may also be in other forms, such as handwriting (e.g. using a Personal Digital Assistant as input device), or spoken language (using a speech recognizer for converting the speech to a representation usable by the system). In a preferred embodiment, the input includes measurement equipment, such as a heart monitor or a blood pressure monitor for providing input data to the system. The output 3 and input 4 may be directly and fixedly connected to the main processing part of the system. Alternatively, the output/input may be separate from the main part 20. For, example, a patient may operate the system from a different location, e.g. through a personal computer or mobile phone. Such a remote terminal is indicated using number 10. The main part 20 and the terminal 10 may exchange data in any suitable form, e.g. via local or wide area communication based on wired or wireless technology. To this end, any suitable protocol may be used, such as SMS, WAP, GPRS, UMTS, Ethernet, etc.

The system also includes a processor 5 that under control of a suitable program, controls the additional functions of the system, such as the input and output, and provides the core functionality of the expert system. The program is preferaly stored in the same storage 2 as used for storing the questions. In a preferred embodiment, the system is used as a front-end for a human expert. It may fully automatically offer assistance for a subset of questions/problems that can be solved by the human expert. In particular, for those questions/problems that cause no irreversible consequences if the system makes a wrong conclusion. As such the system can operate as a first line help/diagnosis system. It relieves the human expert from the simpler cases. For the other case, the system may not offer any assistance, refer the user to an expert, or collect relevant data and automatically transfer the user (and the collected data) to the expert for confirming a hypothesis that the system may not confirm.

Figure 3:
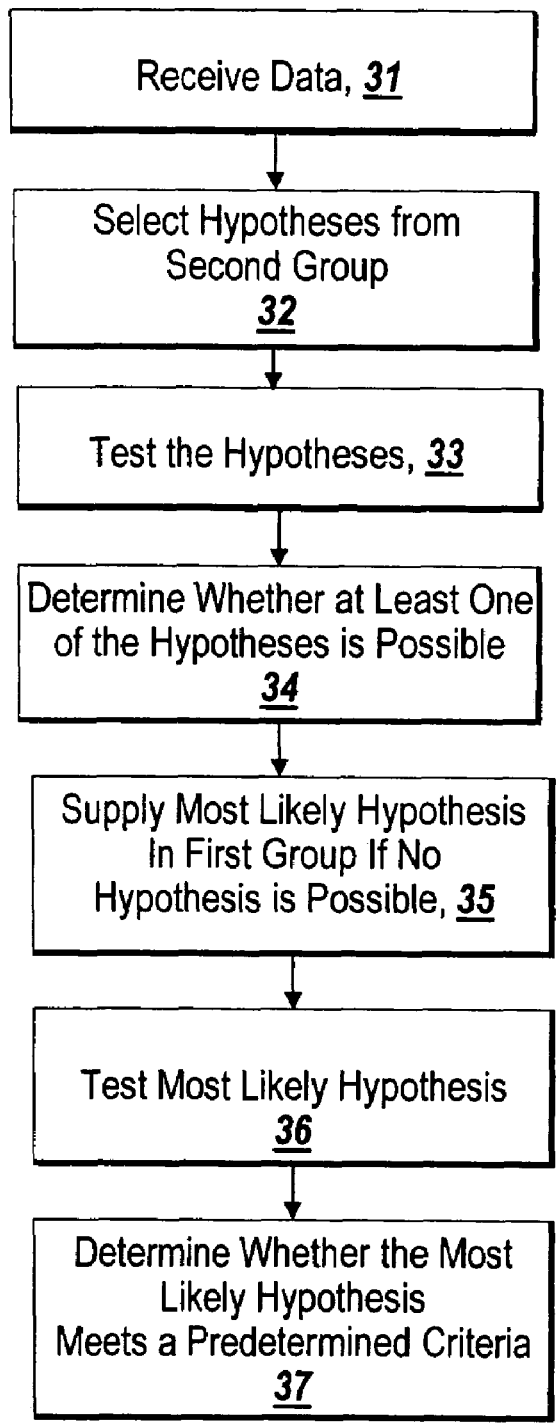
FIG. 3 is a flow chart showing an exemplary process for practicing an embodiment.

According to the invention, the processor 5 is programmed to receive initial data from the user via the input (step 31 in FIG. 3). Usually, the user will provide at least part of this initial data directly to the system (through the input as described above).

The initial data, including the complaint, is the starting point for coming to a diagnosis. For a system that is not capable of giving many different diagnoses, it is preferred that first the complaint is specified and the system confirms that it may be able to issues a diagnosis for the complaint before the user is requested to enter other data necessary to evaluate hypotheses. In this way it can be avoided that the user has to provide unnecessary data. Similarly, it is preferred that a user first provides some general input, like age and sex, before a complaint can be specified. The general data enables the system to compile a list of complaints that may be specified by the user. The complaint list is preferably compiled based on gender and/or age of the user. For example, a complaint 'lower back pain' may normally only be specified by users between 16 and 55 years old. For children and teenagers this is not a normal complaint; for people over 55 without any further questions it can be concluded that the user has to consult a medical expert, since this may indicate cancer. As a further example, complaints relating to menstrual complaints will only be specifiable by females between the ages of 12 and 55 (outside this age range the complaint may occur but is by definition abnormal and requires attention of a medical expert).

Preferably, the system provides the user with a means of selecting a complaint possible for the user. This may be done using drop-down menus from which the user can select a complaint. In a preferred embodiment the user can provide a medical complaint by pointing/selecting a part of a human body using a pointer device, such as a mouse, tracker ball, touch pad, or remote control. This enables a user to enter the complaint with a minimum of interactions. It is possible, as will be described in more detail below, that at least part of the initial data is retrieved from another system, like a medical record system, shown in FIG. 1 using number 10. In the latter situation, the user will normally have to provide some form of identification to the expert system or the medical record system enabling the medical record system to verify that the record (or part of it) may be released for processing by the expert If the first check by the system reveals that for the initial data it can issue at least one diagnosis (i.e. there is a likely diagnosis corresponding to a hypothesis of the first group, i.e. relatively minor, treatable ailments) the user can register in a way usual for computer implemented systems, for example using a login procedure enabling the computer to establish the identity of the user. If the user has not registered before, the system may ask general personal data for creating a patient record, such as a medical insurance number. The system can store this in an own storage, such as storage 2, but may also transfer it to an outside medical record storage system, like record storage system 20, that for example is located at the location of a general practitioner of the user. Such a storage system may communicate with the main part 20 of the system via any suitable interface that preferably supports confidential exchange of information. The interface is indicated using number 25. The record storage swstem 20 may be part of the database of the human expert and though this system 20 data may be supplied to the expert or received from the expert.

The system is preferably directed by an initial complaint that is provided by the user as part of the initial data. Typically, the initial complaint is the medical complaint causing most grievances or is most dominant at that moment, such as fever. The system stores in the storage 2 for each specifiable initial complaint a most likely diagnosis that the system may give. For example, for a complaint running nose the most likely innocent diagnosis is a cold. It may store more diagnoses (21 in FIG. 2) that it may give, preferably each with their likelihood. These hypotheses that the system may give form a first group (22 in FIG. 2) of hypotheses, stored in the storage 2. A basic system may only support the ten most occurring initial complaints. Such a system can serve most of the time approximately 30% of the population for consultations of the general practitioner (GP). With 60 most occurring initial complaints approximately 60% of the people can be served most of the time. By supporting approximately 200 initial complaints most people can be served most of the time. Usually, an initial complaint is related to more than one hypothesis the system may take (forming a first group of hypotheses). For example, an initial complaint of a running nose is related to the hypotheses rhinitis, sinusitis, influenza, etc. In some cases there is a one-to-one relationship between the complaint and hypothesis/diagnosis. In many of these cases, the complaint and diagnosis have the same name. For example, the complaint low back pain relates to the hypothesis/diagnosis low back pain. Storage 2 also stores a collection of hypotheses that the system may not take. These hypotheses form a second group (23 in FIG. 2) of hypotheses. Preferably, the most likely initial hypothesis of the first group is selected based on all initial data, not just the initial complaint. In particular, the hypothesis may also be determined in dependence on the gender and/or age of the user. To this end, the storage 2 may store a table like the one given below. As described above, not all complaints are possible for all other initial data.

| Gender | Age group | Complaint | | Hypothesis | | | |
|---|---|---|---|---|---|---|---|
| | | ID | Description | ID | Description | Group | Likelihood |
| Male | <12 | C1 | Pain or stinging on urinating | M1 | | 2 | Small |
| Male | | C2 | | M2 | | | |
| Female | <12 | C3 | Vaginal loss of blood | F1 | | 2 | Small |
| Female | >1 | C1 | Pain or stinging on urinating | F2 | Cystitis | 1 | High |
| Either | >55 | C4 | Lower back complaints | E1 | | 2 | Small |

In this example, for each complaint an identifier and a textual description is stored. For each hypothesis an identifier (e.g. number, possibly complemented a mark that distinguishes between the sex and/or age group), a textual description, and a likelihood is stored (based on the initial data which in this example is: gender, age group, and complaint). The likelihood may be given as a percentage, but it may also take any other suitable form that enables the system to rank the hypotheses (e.g. a sequential number, or a choice from options, like small, average, high). Also an indication of the group to which the hypothesis belongs (i.e. first group or second group) is stored. The first and second group may be stored separately, but may also be stored in one collection as is shown in the table above. Using such a shared storing, the groups may be identifiable using a label (as shown using the column 'Group.

No'), that may be implemented using a one-bit indicator indicating the first or second group. The distinction between the groups may also be implicit, for example in the outcome following a confirmation of the hypothesis.

Instead of evaluating all possible hypotheses (those of the first and second group) that are possible for the initial data, according to the invention the system first determines a list of hypotheses of the second group that match the initial data, i.e. possible hypotheses that the system may not take. To this end, the processor 5 is programmed to select all hypotheses from the second group that are possible in dependence on the initial data (step 32 in FIG. 3). Using a table like the one described above, the processor can perform this by finding all rows in the tables with the first three columns matching the gender, age group and initial complaint specified by the user and using the fifth column to select only hypotheses from the second group. Having established the list of hypotheses of the second group, the system tries to eliminate each of these hypotheses by testing the hypotheses using questions.

To this end, the storage 2 stores a collection of questions for testing hypotheses. The questions may be arranged in question sets, each of at least one question, where a question set contains the questions for testing an associated hypothesis. According to the invention the system makes a distinction between testing hypotheses of the first and second disjoint group of hypotheses. For each hypothesis of the second group the system stores a respective associated question set for rejecting the hypothesis. In a basic implementation of the system, no additional questions need to be stored for the hypotheses of the first group. In a preferred embodiment, the storage 2 stores for at least one hypothesis of the first group a respective associated question set for confirming the hypothesis. Typically, the questions in a question set are stored sequentially. The following table shows an example of how information on questions and answers may be stored, in this example for hypothesis M1.

| Questions | | Answers | | | | | |
|---|---|---|---|---|---|---|---|
| | | Answer 1 | | Answer 2 | | Answer 3 | |
| ID | Description | ID | Description | ID | Description | ID | Description |
| M1-1 | | M1-1-1 | Yes | M1-1-2 | No | | |
| M1-2 | | M1-2-1 | Yellow | M1-2-2 | Green | M1-2-3 | Purple |
| M1-3 | | | | | | | |

Each question may be stored using several fields, such as a unique identifier, a textual representation of the question, and answers that may be specified by a user. The question identifier may simply be a number, enabling a human expert to review and identify the questions. Preferably, the questions are uniquely identified over all sets of questions. For each question, the system stores at least two possible answers, like a yes/no answer. Also more than two answers may be possible like the answers to a question involving a color may be yellow, green and purple. Preferably, the answer field of each question includes for each specifiable answer a textual representation of the answer (e.g. 'green') and an identifier. The answer identifiers may be sequentially numbered, e.g. the identifier for yellow is 1, for green is 2 and for purple is 3. Of course any suitable identifier may be used. The answer identifier in combination with the question identifier uniquely identifies each answer. In the example shown in the table the answer identifier already includes the question identifier. The table shows a maximum of three different answers. It will be appreciated that more answers may be specifiable also.

The processor 5 is programmed to test the selected hypotheses (step 33 in FIG. 3. It does this by retrieving a question of the question set of a selected hypothesis from the storage, provide this question to the user via the output of the system and receive an answer to the question from the user via the input. The processor may also provide to the user an overview of answers the user may give. The processor is also programmed to evaluate the possibility of the hypothesis in view of the given answer(s). If it detects that a hypothesis is not possible any more, it deselects the hypothesis (in the sense that it for the time being discontinues testing and considering this hypothesis). In a simple implementation, the processor retrieves each question set (for respective selected hypotheses of the second group) sequentially and sequentially issues all questions of the set until:

generated automatically, for example by attaching attributes to the questions, like a subject. The system can then sort questions of selected sets based on these attributes. It is also possible to enabling links between questions to be established, so that the system ensures that linked questions in selected sets are provided in the sequence specified by the linking.

An effective way of ensuring a logical behavior of the system is storing predetermined question lists in the storage 2 that have been compiled by a human expert based on hypotheses of the second group that are possible for a specific set of initial data. The following table shows an example of one question list of eight questions, numbered one to 8 in the first column.

| | | Question list X | | | |
|---|---|---|---|---|---|
| | Answer sequence | Answer keys in database | | | |
| Question ID | A0 | K1 | K2 | K3 | K4 |
| 1 | 1 | * | 1 | 1 | 1 |
| 2 | 2 | * | * | * | * |
| 3 | 2 | * | 3 | 3 | 3 |
| 4 | * | * | 2 | * | * |
| 5 | 1 | 5 | | 2 | 4 |
| 6 | 5 | | | * | 1 |
| 7 | 2 | | | * | |
| 8 | 1 | | | * | |
| Action/conclusion, Diagnosis | | Conclusion W, to GP | Exit to question list Y | Diagnosis V | Conclusion Z | an answer indicates that the hypothesis is likely and can not be rejected, or an answer indicates that the hypothesis is not possible (step 34 in FIG. 3).

If all hypotheses have been rejected, the most likely hypothesis of the first group may be issued to the user (step 35 in FIG. 3). Otherwise, testing can stop as soon as one hypothesis of the second group is likely or can not be ruled out by the system. In this case, no diagnosis can be issued. Instead, the system may recommend the user to consult a medical expert or automatically transfer the interaction to the medical expert (or arrange that an appointment with the medical expert is made). The question sets may be issued in decreasing likelihood of the associated hypothesis (i.e. starting with the most likely one and ending with the least likely one).

Preferably, individual questions and their answers can be shared between question sets. Instead of providing the individual question sets of the selected hypotheses of the second group sequentially to the user, it is preferred to compile one coherent list of questions that covers all question sets of the selected hypotheses. In this way, it is simple to eliminate the same questions that occur in multiple sets. Moreover, questions of different sets that relate to the same subjects can be grouped together, increasing the logical behavior of the systems towards the user. As an example, question sets Q1 and Q10 may share same question 121. It is possible that Q10 (but not Q1) includes a question 122 that collects more detail on the subject covered 121. If both sets Q1 and Q10 need to be tested, it is preferred that question 121 is followed by 122 and that not first question 121 is issued and much later question 122 is issued. Such a logical behavior of the system may be The exemplary question set is a question set designed for testing a most likely diagnosis of rhinitis. The table shows that the question list covers four different hypotheses k1 to k4. As an example:

Question 1: What is the color of the nasal mucus?
Possible answers: 1 yellow, 2 green; 3: colorless
Question 2: Does your throat hurt?
Possible answers: 1 yes; 2 no The question set for k1 is formed by question 6; the set for k2 includes questions 1, 3, and 4; the set for k3 consists of questions 1, 3, and 5; the set for k4 consists of the questions 1, 3, 5 and 6. The last row of the table indicates the actions taken by the system in response to confirming a hypothesis (at least for as far as possible based on the question set). k1, k2 and k4 are the only hypotheses of the second group that matched certain initial data. If k1 can not be rejected, the action/conclusion of the system may be to give the user a message like "the symptoms you've described are likely to fit with an ailment that needs attention from a medical expert. Make an appointment with a GP". If k2 is confirmed, conclusion W is taken (e.g. disease k2, for example sinusitis can not be ruled out) and the user is directed to the general practitioner. If k4 can not be rejected, conclusion Z is given. This may be "Diagnosis: tracheitis k4: from your answers it is clear that you are very concerned. Although there are no indications that you have a serious ailment, it is advisable to consult your GP if your concerns stay". If hypothesis k2 (sinusitis) is possible, the system is able to test this further. To this end, it retrieves a further question set Y for specifically further testing of hypothesis k2 with the aim of eliminating and/or confirming k2. If k2 is positively confirmed, the data will normally be provided to a medical expert for further attention. If the system comes to the conclusion that none of the hypotheses k1, k2 or k4 are possible it may in principle confirm the most likely hypothesis of the first group that matched the initial data. Preferably, also answers to questions issued during the testing of the hypotheses are used to confirm the most likely hypothesis of the first group. The table illustrates an effective way of doing this. The most likely hypothesis of the first group is indicated as k3. Question 1, 3 and 5 of the question list also provide valuable feedback for hypothesis k3. Certain answers to these questions will increase the confidence in issuing this diagnosis, whereas other answers to this question may indicate that this hypothesis is not possible. In the latter case, the processor is programmed to retrieve another (the then most likely) hypothesis of the first list that matches the initial data (and preferably also the answers to the questions).

Having successively rejected all hypotheses of the second group, and possibly based on the answers increased the confidence of a most likely hypothesis, the system may be able to further test the most likely hypothesis (step 36 in FIG. 3). To this end, the memory 2 stores for a hypothesis of the first group a respective associated question set for confirming the hypothesis. The processor 5 is programmed to, if after the testing no hypothesis of the second group is selected, further test the most likely hypothesis by providing the associated question set from the memory to the user via the output. It receives further answer(s) from the user via the input, and determines whether the most likely hypothesis meets a predetermined criterion (step 37 in FIG. 3). The criterion may, for example be, that it matches at least one predetermined answer key or that a likelihood, in view of the answers, is above a defined level or higher than for other hypotheses. It provides an outcome of the analysis to the user or to a human expert (or system used by such an expert). If the further answers indicate that the hypothesis must be rejected, the system may test the then most likely hypothesis of the first group using questions aimed at confirming the hypothesis. Since in many cases, a most likely hypothesis will be confirmed, it is possible to sequentially test those hypotheses without requiring too many questions in most cases. It is also possible to create a combined question list from several question sets for hypotheses of the first group. By first testing hypotheses to be rejected, the question list for that will be smaller than for testing all hypotheses. Moreover, the number of answers keys is much smaller. Optionally in a second test round questions can be added that not yet have been issued and are required for confirming hypotheses of the second group. For this second round of testing (that may not be needed at all) the number of keys (as will be described in more detail below) can again be much smaller since only keys for hypotheses of the first group need to be implemented. According to the invention, the testing of the hypotheses of the second group does not include all questions for confirming hypotheses of the first group. Alternatively or additionally, the answer sequence of a user is during the testing of the hypotheses of the second group not compared to at least one answer sequence (key) that confirms a hypothesis of the first group. In this way the number of questions (and thus key lengths) and/or number of keys to be compared can be reduced. Both measures significantly increase the performance of the system and reduce storage space.

The table also illustrates a effective way of confirming or rejecting a hypothesis, based on using so-called keys. According to the invention, the system only needs to store keys that are coded for rejecting the hypotheses of the first list (in this example: those that indicate that hypotheses k1, k2 or k4 are possible). Column 2, indicated as A0, shows the answers given by a user. The keys may be designed only for a specific question set that belong to a hypothesis. In the example, each key is designed to verify that the corresponding hypothesis can be confirmed where the set of questions may also include questions for testing other hypotheses. As a consequence certain questions are irrelevant for testing hypothesis. This is indicated by a '*' in the table. This represents a wildcard in the columns for the hypotheses k1 to k4. A user may also provide no answer o question, e.g. skip the question or provide an answer 'don't know'. This is represented by a wildcard '*' in the answer column A0 (in this example: answer to question 4). This implies that entry 4 of each key will not be compared. It will be appreciated that normally answers to questions are not ignored by the system. Since the intention is to 'safely' eliminate hypotheses of the second group, it is preferred to interpret a 'don't' type of answer as one of more of the other answers that may confirm a hypothesis of the second group. For example, if the answer to question 'Is there blood in your nose?' is 'don't know', this will be interpreted as 'yes'. Preferably, storage 2 also stores the keys. The keys may be stored in database, together with the question sets, possible answers to the questions, and specific compilations of questions lists for testing more that one hypothesis using only one list. The storage (e.g. database) preferably also stores for each key the action/conclusion to be made if the key matches the answers given by a user (i.e. the hypothesis is possible). The actions/conclusions are shown in the last row.

The table also shows some optimizations of the system according to the invention. Preferably, individual answers are evaluated immediately after they are given. This can imply that the questioning can be stopped if an answer(s) confirms that hypothesis of the second group can not be rejected. In the example, if the answer to question 6 is 5, then hypothesis k1 can not be rejected. The questioning can stop and the user directed to the general practitioner. It will be appreciated that fields in the table that are irrelevant if answers are immediately processed need not to be filled in. Alternatively, they may be filled-in with wildcards. Examples of such fields are the fields for question 7 and 8 of k1 and 5 to and including 8 for K2. If so desired, the 'irrelevant' questions may nevertheless be asked. The answers to these questions can be used to alter the weights (i.e. likelihood) of the corresponding conclusion. The answers may also indicate that also another hypothesis is possible and even more likely. Preferably, if more than one hypothesis is likely, the one with the most weight is presented (or presented with most emphasis). If two or more hypotheses have a substantially equal likelihood, the one that completes first is given most emphasis.

The table shows for k2 a further strength. Having answered 1 to question 1, 3 to question 3 and 2 to question 4, the system comes to the conclusion that it can not yet reject hypothesis k2. However, the system may be able to do this by using a further question set Y specifically designed for rejecting k2 only. In response to the answer 2 to question 4, it loads the question set Y. Together with question set Y it loads one or more keys for testing the answers to question set Y and actions if the keys match. Normally at least one of the keys will lead to the conclusion that k2 is possible (and most likely that the user must seek medical attention). As such, the system is able to organize question sets and question lists in a tree structure, where a branch of a tree is one question set or list. During the evaluation of a set/list an answer to a question may result in loading of a further set/list, forming a sub-branch in the tree. Several questions in one set may have this effect, all leading to different sub-branches. A sub-branch can again have further sub-branches. Starting at the root of the tree, the initial data triggers is stat the evaluation at the most likely branch of the tree. Answers to questions may result in going down sub-branches are returning to higher branches. It is even possible to jump from one branch to another branch, that may be hierarchically higher, lower or at a same level parallel to the branch, by linking branches. Preferably, in dependence on an answer the system is operable to skip one or more questions of a questions set/list. For example, if a user has indicated that he/she has no temperature, subsequent questions on the height and duration of the temperature can be skipped. This can be effected by linking answers to an individual question to be issued next, that may be a first question of another question set, but may also be a question somewhere in the same set (or another set).

Confirmation of a hypothesis of the first group may result in informing the user of the diagnosis and recommending a treatment that can be done by the user without further medical attention, whereas a confirmation of a hypothesis of the second group may result in urging the user to consult a medical expert.

The answer keys are preferably entered into the storage of the system using templates that enable an operator to indicate that for certain questions multiple answers code for rejection of the hypothesis being tested. The keys are then generated automatically using the template. The following table shows an example of how such a template may operate.

| Question ID | Answer ID | Exit criterion | Number of hits |
|---|---|---|---|
| 1 | 1 |   | 2 |
|   | 2 | X |   |
|   | 3 | X |   |
| 2 | 1 | X |   |
|   | 2 |   |   |
| 3 | 1 | X |   |
|   | 2 |   |   |
|   | 3 | X |   |
|   | 4 |   |   |

Assuming that a question set includes the indicated 3 questions and for each of the questions the indicated answers, a human operator can indicate in the third column which of the answers contributes to diagnosis/conclusion/action X. In this example, this may result in generating four keys, since two answers of question 1 and two answers of question 3 contribute, giving the following four key sequences: (2, 1, 1), (3, 1, 1), (2, 1, 3), and (3, 1, 3). The fourth column shows that the user may also indicate how many 'hits' (i.e. answers given by a user that corresponds to X) are required before X is issued by the system. During operation, the system initializes for each hypothesis a counter to the value specified by the operator in column four. Each time a hit occurs for the hypothesis, its counter is lowered by one, until it reaches zero. At that moment, the diagnosis can be taken. In the example, if X has two hits, the hypothesis may be taken. This is before any of the four keys has a complete match. According to the invention, the four key can then be all combined and the actual matching of answers to the keys in combination with the number of hits determines that a hypothesis can be taken. This further reduces the number of keys and can also reduce the number of questions that need to be issued. As an example, a diagnosis allergic rhinitis' may me taken if seven out of the following eight symptoms are present:

a running nose with clear mucus
from both nostrils
sneezing
facial itch
watery eyes
caused by: pollen or dust or (house) animals
more frequent than 3 times a year
symptoms present for two weeks or longer In most cases a medical advice given is only valid for a certain period, mostly seven days. During this period most complaints for which the system can issue a diagnosis should have gone. In a preferred embodiment, the system takes the initiative to contact the user after such a predetermined period (that may be complaint-specific) and remind the user that the complaint should have gone. The reminder may take place via email. If the complaint has not gone the user may decide to seek assistance from a human medical expert. The reminder may include such an advice. It is also possible that the user contacts the system again. Preferably, the initial data supplied to the system contains sufficient information (like a user name) for the system, to determine that the user is a revisiting user. If the complaint is the same, the system can based on data stored in its medical records determine the duration of the complaint and adjust its advice accordingly. For new users, the system may ask for information on how long the complaint already exists. If the system detects that a complaint has lasted unusually long, preferably the system also automatically informs a human expert. Advantageously, the system is operative to use meta-data as part of testing the hypothesis or as part of selecting the hypotheses to be tested. Such meta-data may include the frequency of a complaint. For example, if a user contacts a general practitioner more than four times a year with a complaint of a running nose/cold, the diagnosis is more likely not an ordinary cold, but might be an allergy. As a further example, a recurring cystitis in girls of age 1 to 5 can point to underlying pathology. Persons by whom on at least 3 different occasions a diastolic blood pressure of >90 mm Hg is measured do most likely have high blood pressure. A single measurement has no predictive value (it can be caused by stress or other external factors). Similarly, a combination of certain drug can cause side effects which can account for certain complaints.

In a preferred embodiment, the system is used to increase the efficiency of a general practitioner (GP). Research shows that more than 70% of patients that go to the GP can be helped by, for example, a nurse or assistant using well-designed protocols. The system according to the invention comes equipped with such protocols in the form of the question sets and the automatic selection of hypotheses to be tested in dependence on the initial data. The system may be operated under control of the nurse and as such give a protocolled judgment of the actual situation and the system can indicate which additional information, such as physical examinations, must be performed or retrieved, e.g. from the medical records of the patient. This information may be retrieved from an own patient database, or via email/telephone b retrieved from other medical records, e.g. from a specalist's record or chemist's records. In this way in many case an adequate diagnosis can be obtained or preparatory work being done without the GP having to see the patient in person. This leads to a significant time saving and may halve the average time of a consultation.

In the case that the system concludes that the complaint is too complicated (i.e. it does not support the complaint at all, it has no hypothesis of the first group that matches the complaint, or it can not reject a hypothesis of the second group), the patient can be referred to one of the practice GPs. The data (such as the initial data and question/answers, where necessary complemented by data from medical records and automatically obtained measurements) may then presented to the GP to enable the GP to quickly grasp the situation and see what most likely is the case and what further questions/answers are required to confirm this. The system preferably also indicates hypotheses of the second group to the GP that can not be ruled out. Preferably, the expert system establishes contact with the computer system(s) of the GPs practice or other medical specialist involved in the process to draw the GP's/specialist's attention to that fact that such a hypothesis must be checked. The medical expert is presented with a (summary of) the relevant complaint and reasons why the most likely hypothesis of the first group can not be confirmed (yet). Preferably, such data can be accessed by the expert with a single activation of a button or link/menu. Advantageously, the system also provides the expert with a differential diagnostical list: a list of possible diagnoses in the order of likelihood. The most likely hypothesis of the first group is presented first (e.g. headache) followed by the hypothesis of the second group that could not yet be ruled out (e.g. brain tumor). Preferably also a list with information lacking to come to the conclusion of an ordinary headache is preferably presented. In many cases the medical expert can obtain the lacking information via a few directed questions to the patient. Mostly, the patient need not visit the expert but the information can be retrieved through the phone of via email. Based on the additional information the expert can confirm or reject the most likely diagnosis. If an additional medical test or examination is required this can usually be performed by a practice nurse. The nurse can enter the result in the records of the system and transfer control back the medical expert.

In a preferred embodiment, the system is also able to communicate or provide data to interested third parties (obviously taking privacy and security regulations into account). As an example, the system may generate statistical information for medical insurance companies or research institutes.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The words "comprising" and "including" do not exclude the presence of other elements or steps than those listed in a claim. The invention can be implemented by means of hardware comprising several distinct elements, and by means of a suitably programmed computer. Where the system/device/apparatus claims enumerate several means several of these means can be embodied by one and the same item of hardware. The compute program product may be stored/distributed on a suitable medium, such as optical storage, but may also be distributed in other forms, such as being distributed via the Internet or wireless telecommunication systems.

The invention claimed is:

1. A computer-implemented expert system including:
   a memory for:
      storing a plurality of hypotheses, where the hypotheses are arranged in at least a first and second disjoint group of hypotheses, wherein the first group of hypotheses includes hypotheses that may be taken by the system and the second group includes hypotheses that may not be taken by the system; and
      storing questions for rejecting hypotheses of the second group; an output for supplying questions from the memory;
   an input for receiving initial data and answers to outputted questions;
   a processor programmed to:
      select questions from the stored questions for those hypotheses from the second group that are possible in dependence on the initial data;
      determine from at least one answer received in response to outputting the selected questions whether at least one of the hypotheses of the second group is possible by comparing received answers to a predetermined answer sequence stored in or derivable from the memory; and
      in response to determining that no hypothesis of the second group is possible, supply via the output a most likely hypothesis of the first group in dependence on at least the initial data,
   wherein the expert system is used for medical diagnosis, the initial data includes a health complaint,
   the second group of hypotheses containing medical diagnoses that require attention of a medical expert,
   the first group of hypotheses containing medical diagnoses that do not require any medical attention or can be cured or treated without assistance of a medical expert, and
   the processor is programmed to select the questions in dependence on the health complaint.

2. An expert system as claimed in claim 1, wherein the memory stores for each hypothesis of the second group a respective associated question set for rejecting the hypothesis; the processor being programmed to select all hypotheses from the second group that are possible in dependence on the initial data and to perform the selection of questions by combining question sets of selected hypotheses of the second group.

3. An expert system as claimed in claim 1, wherein the processor is programmed to supply via the output an indication that no hypothesis can be made in response to determining that at least one hypothesis of the second group is possible.

4. An expert system as claimed in claim 1, wherein the processor is programmed to terminate outputting questions in response to determining that at least one hypothesis of the second group is possible.

5. An expert system as claimed in claim 1, wherein the memory stores for at least one hypothesis of the first group a respective associated question set for confirming the hypothesis; and wherein the processor is programmed to, in response to determining that no hypothesis of the second group is possible, and the most likely hypothesis of the first group is associated with a question set:
   output questions of the associated question set;
   determine whether the most likely hypothesis meets a predetermined criterion in dependence on at least one further answer; and
   provide an outcome of the determination.

6. An expert system as claimed in claim 1, wherein the memory stores for at least one hypothesis of the second group a respective associated further question set for confirming the hypothesis; and wherein the processor is programmed to, in response to determining that the hypothesis of the second group is possible:
   output questions of the associated question set;
   determine whether the hypothesis of the second group meets a predetermined criterion in dependence on at least one further answer; and
   provide an outcome of the determination.

7. An expert system as claimed in claim 1, wherein the processor is programmed to update the selection of questions during testing of the questions in dependence on one or more received answers.

8. An expert system as claimed in claim 1, wherein the processor is programmed to perform the determining whether a hypothesis of the second group is possible also in dependence on at least one answer received for earlier questions and/or the initial data.

9. An expert system as claimed in claim 1, wherein the processor is programmed to determine a most likely hypothesis of the first group also in dependence on one or more received answers.

10. An expert system as claimed in claim 1, wherein the processor is programmed to transfer control to a human expert.

11. An expert system as claimed in claim 1, wherein the expert system is used as a medical diagnosis system; the expert system including a communication interface for exchanging data regarding a medical record of a patient from a storage system for storing medical records of patients; the processor being programmed to retrieve answers to questions from the medical record and/or store data in the medical record.

12. An expert system as claimed in claim 3, wherein the processor is programmed to transfer the control in response to determining that the selected hypothesis meets the predetermined criterion.

13. An expert system as claimed in claim 9, wherein the processor is programmed to transfer the control in response to determining that the selected hypothesis meets the predetermined criterion.

14. A medium holding instructions executable in a computer, the instructions causing a processor to perform the steps of:

receiving initial data via an input;
selecting from a memory that stores:
    a plurality of hypotheses, where the hypotheses are arranged in at least a predetermined first and second disjoint group of hypotheses, wherein the first group of hypotheses includes hypotheses that may be taken by the processor and the second group includes hypotheses that may not be taken by the processor, and
    questions for rejecting hypotheses of the second group, questions for those hypotheses from the second group that are possible in dependence on the initial data;
determining from at least one answer received in response to outputting the selected questions whether at least one of the hypotheses of the second group is possible by comparing received answers to a predetermined answer sequence stored in or derivable from the memory; and
in response to determining that no hypothesis of the second group is possible, supplying via the output a most likely hypothesis of the first group in dependence on at least the initial data,
wherein the processor is used for medical diagnosis, the initial data includes a health complaint,
the second group of hypotheses containing medical diagnoses that require attention of a medical expert,
the first group of hypotheses containing medical diagnoses that do not require any medical attention or can be cured or treated without assistance of a medical expert, and
the processor is programmed to select the questions in dependence on the health complaint.

* * * * *